(12) United States Patent
Mikkelsen et al.

(10) Patent No.: US 9,408,475 B2
(45) Date of Patent: Aug. 9, 2016

(54) SUPPORT CUSHIONS AND METHODS FOR CONTROLLING SURFACE TEMPERATURE OF SAME

(71) Applicant: Tempur-Pedic Management, LLC, Lexington, KY (US)

(72) Inventors: Tom Mikkelsen, Lexington, KY (US); Kelly Wood Chandler, Gate City, VA (US)

(73) Assignee: Tempur-Pedic Management, LLC, Lexington, KY (US)

( * ) Notice: Subject to any disclaimer, the term of this patent is extended or adjusted under 35 U.S.C. 154(b) by 0 days.

(21) Appl. No.: 14/379,820

(22) PCT Filed: Oct. 18, 2012

(86) PCT No.: PCT/US2012/060775
§ 371 (c)(1),
(2) Date: Aug. 20, 2014

(87) PCT Pub. No.: WO2014/062185
PCT Pub. Date: Apr. 24, 2014

(65) Prior Publication Data
US 2015/0033474 A1 Feb. 5, 2015

(51) Int. Cl.
*A47C 21/04* (2006.01)
*H05B 3/20* (2006.01)
*A47C 7/74* (2006.01)
(Continued)

(52) U.S. Cl.
CPC ............... *A47C 21/044* (2013.01); *A47C 7/744* (2013.01); *A47C 7/748* (2013.01); *A47C 21/048* (2013.01); *A47C 27/00* (2013.01); *A47G 9/1036* (2013.01); *H05B 3/20* (2013.01)

(58) Field of Classification Search
CPC .... A47C 21/04; A47C 21/042; A47C 21/044; A47C 21/048; A47C 7/72; A47C 7/74; A47C 7/742; A47C 7/748
USPC ........... 5/630, 636, 652, 655.9, 421, 740, 953
See application file for complete search history.

(56) References Cited

U.S. PATENT DOCUMENTS 2,585,517 A * 2/1952 Tolen ................................ 5/284
3,132,688 A * 5/1964 Nowak ............................ 602/14
(Continued)

FOREIGN PATENT DOCUMENTS

| CN | 2864512 | 1/2007 |
|----|---------|--------|
| CN | 201468654 | 5/2010 |

(Continued)

OTHER PUBLICATIONS

Patent Cooperation Treaty, International Search Report and Written Opinion, Jul. 17, 2013, 7 pgs.

*Primary Examiner* — David E Sosnowski
*Assistant Examiner* — Ifeolu Adeboyejo

(57) ABSTRACT

A support cushion for providing individualized heating and cooling to a user resting on the support cushion is provided. The support cushion includes a body supporting portion, a plurality of thermoelectric elements positioned and configured to selectively provide heating or cooling of the body supporting portion, and a heat dissipating portion that is comprised of a thermally-absorbent material and is operably connected to the thermoelectric elements. Methods of controlling a surface temperature of a support cushion are also provided.

28 Claims, 10 Drawing Sheets

(51) Int. Cl.
*A47G 9/10* (2006.01)
*A47C 27/00* (2006.01)

(56) References Cited

U.S. PATENT DOCUMENTS

| | | | |
|---|---|---|---|
| 3,136,577 A * | 6/1964 | Richard | 297/180.11 |
| 3,248,777 A | 5/1966 | Stoll | |
| 3,266,064 A * | 8/1966 | Figman | 5/726 |
| 3,648,469 A * | 3/1972 | Chapman | 62/3.5 |
| 3,885,258 A * | 5/1975 | Regan | 5/727 |
| 4,141,585 A * | 2/1979 | Blackman | 297/180.14 |
| 4,162,393 A * | 7/1979 | Balboni | 219/217 |
| 4,470,263 A | 9/1984 | Lehovec et al. | |
| 4,825,488 A * | 5/1989 | Bedford | 5/726 |
| 4,866,800 A * | 9/1989 | Bedford | 5/652.1 |
| 4,930,317 A | 6/1990 | Klein | |
| 5,010,608 A | 4/1991 | Barnett et al. | |
| 5,097,828 A | 3/1992 | Deutsch | |
| 5,117,638 A | 6/1992 | Feher | |
| 5,344,436 A | 9/1994 | Fontenot et al. | |
| 5,528,779 A | 6/1996 | Lee et al. | |
| 5,653,741 A | 8/1997 | Grant | |
| 5,800,480 A * | 9/1998 | Augustine et al. | 607/96 |
| 5,800,490 A | 9/1998 | Patz et al. | |
| D400,313 S | 10/1998 | Chatwell | |
| 5,889,923 A | 3/1999 | Lee et al. | |
| 6,023,932 A | 2/2000 | Johnston | |
| 6,062,641 A | 5/2000 | Suzuki et al. | |
| 6,109,256 A | 8/2000 | Sardi | |
| 6,128,795 A | 10/2000 | Stanley et al. | |
| 6,220,659 B1 | 4/2001 | McDowell et al. | |
| 6,256,818 B1 | 7/2001 | Hughes | |
| 6,263,530 B1 | 7/2001 | Feher | |
| 6,378,948 B1 | 4/2002 | Macher et al. | |
| 6,428,564 B1 | 8/2002 | Ferguson | |
| D469,998 S | 2/2003 | Feeney | |
| 6,524,331 B1 * | 2/2003 | Kohout et al. | 607/96 |
| 6,546,576 B1 | 4/2003 | Lin | |
| 6,568,006 B1 | 5/2003 | Hyland | |
| 6,581,224 B2 | 6/2003 | Yoon | |
| 6,582,456 B1 | 6/2003 | Hand et al. | |
| 6,596,018 B2 | 7/2003 | Endo et al. | |
| 6,606,754 B1 * | 8/2003 | Flick | 5/421 |
| 6,619,737 B2 * | 9/2003 | Kunkel et al. | 297/180.14 |
| 6,626,488 B2 * | 9/2003 | Pfahler | 297/180.11 |
| 6,653,607 B2 * | 11/2003 | Ellis et al. | 219/528 |
| 6,664,512 B2 | 12/2003 | Horey et al. | |
| 6,689,155 B2 | 2/2004 | Gammons et al. | |
| 6,699,266 B2 | 3/2004 | Lachenbruch et al. | |
| 6,701,552 B2 | 3/2004 | Suzuki et al. | |
| 6,711,767 B2 | 3/2004 | Klamm | |
| 6,770,085 B1 | 8/2004 | Munson | |
| 6,792,671 B1 | 9/2004 | Oberg | |
| 6,803,543 B2 | 10/2004 | Argersinger et al. | |
| 6,826,792 B2 | 12/2004 | Lin | |
| 6,839,922 B1 | 1/2005 | Foggett et al. | |
| 6,855,158 B2 | 2/2005 | Stolpmann | |
| 6,871,366 B2 | 3/2005 | Cho | |
| 6,918,144 B2 | 7/2005 | Friedman | |
| 6,924,467 B2 | 8/2005 | Ellis et al. | |
| 6,957,454 B1 | 10/2005 | Newton | |
| 6,967,309 B2 * | 11/2005 | Wyatt et al. | 219/217 |
| 7,036,575 B1 | 5/2006 | Rodney et al. | |
| 7,117,816 B2 | 10/2006 | Behnke et al. | |
| 7,176,419 B2 | 2/2007 | Ellis et al. | |
| 7,178,183 B2 | 2/2007 | Cho | |
| 7,181,787 B2 | 2/2007 | Wu | |
| 7,196,289 B2 | 3/2007 | Ellis et al. | |
| 7,240,386 B1 * | 7/2007 | McKay et al. | 5/724 |
| 7,272,936 B2 | 9/2007 | Feher | |
| 7,278,179 B2 | 10/2007 | Schneider | |
| 7,543,344 B2 | 6/2009 | Augustine et al. | |
| 7,546,653 B2 | 6/2009 | Ye | |
| 7,765,811 B2 * | 8/2010 | Hershberger et al. | 62/3.5 |
| 7,832,032 B2 | 11/2010 | Haislip | |
| 7,908,687 B2 | 3/2011 | Ward et al. | |
| 7,996,936 B2 | 8/2011 | Marquette et al. | |
| 8,065,763 B2 | 11/2011 | Brykalski et al. | |
| 8,074,307 B2 | 12/2011 | Spratley | |
| 2002/0124312 A1 * | 9/2002 | Yoon | 5/421 |
| 2003/0047550 A1 | 3/2003 | Horey et al. | |
| 2003/0088300 A1 | 5/2003 | Vester | |
| 2003/0229385 A1 * | 12/2003 | Elkins | 607/104 |
| 2004/0040946 A1 | 3/2004 | Nation | |
| 2005/0086739 A1 * | 4/2005 | Wu | 5/423 |
| 2005/0278863 A1 * | 12/2005 | Bahash et al. | 5/726 |
| 2006/0278628 A1 | 12/2006 | Foggett et al. | |
| 2007/0107134 A1 | 5/2007 | Pittman | |
| 2007/0272673 A1 | 11/2007 | Keane | |
| 2007/0277312 A1 * | 12/2007 | Garrigues | 5/420 |
| 2007/0277313 A1 * | 12/2007 | Terech | 5/421 |
| 2008/0000025 A1 | 1/2008 | Feher | |
| 2008/0028517 A1 | 2/2008 | Schmidt | |
| 2008/0168605 A1 | 7/2008 | Wolske | |
| 2008/0306577 A1 | 12/2008 | Schock et al. | |
| 2009/0000031 A1 | 1/2009 | Feher | |
| 2009/0078690 A1 | 3/2009 | Lee et al. | |
| 2009/0119846 A1 * | 5/2009 | Meyer et al. | 5/709 |
| 2010/0005572 A1 | 1/2010 | Chaplin | |
| 2010/0107334 A1 | 5/2010 | Yi | |
| 2010/0212088 A1 * | 8/2010 | Deighan | 5/421 |
| 2010/0287701 A1 | 11/2010 | Frias | |
| 2010/0293715 A1 | 11/2010 | Sakamoto et al. | |
| 2010/0319125 A1 | 12/2010 | Ko | |
| 2011/0000018 A1 | 1/2011 | Kirchhoff | |
| 2011/0035880 A1 | 2/2011 | Cole et al. | |
| 2011/0041246 A1 | 2/2011 | Li et al. | |
| 2011/0067178 A1 | 3/2011 | Lee | |
| 2011/0107514 A1 | 5/2011 | Brykalski et al. | |
| 2011/0296611 A1 | 12/2011 | Marquette et al. | |
| 2012/0017376 A1 * | 1/2012 | Mikkelsen et al. | 5/726 |
| 2012/0060885 A1 * | 3/2012 | Makansi et al. | 136/206 |
| 2012/0131748 A1 | 5/2012 | Brykalski et al. | |
| 2012/0198616 A1 * | 8/2012 | Makansi et al. | 5/423 |

FOREIGN PATENT DOCUMENTS

| | | |
|---|---|---|
| CN | 201757539 | 3/2011 |
| DE | 202004013089 U1 | 11/2004 |
| JP | 9-276315 A | 10/1997 |
| JP | 2000300411 A | 10/2000 |

* cited by examiner

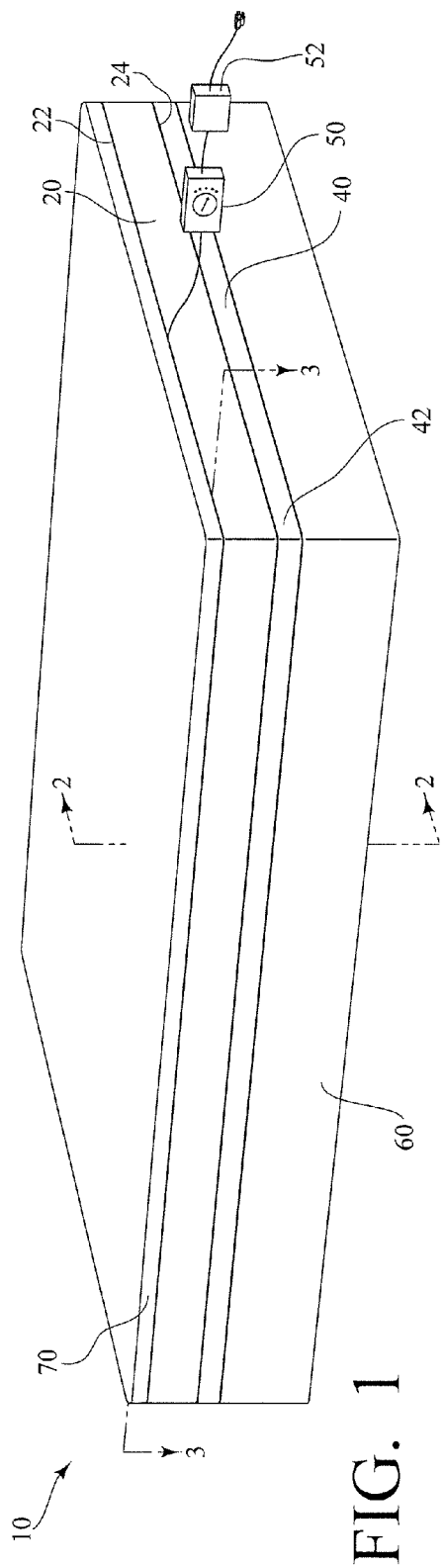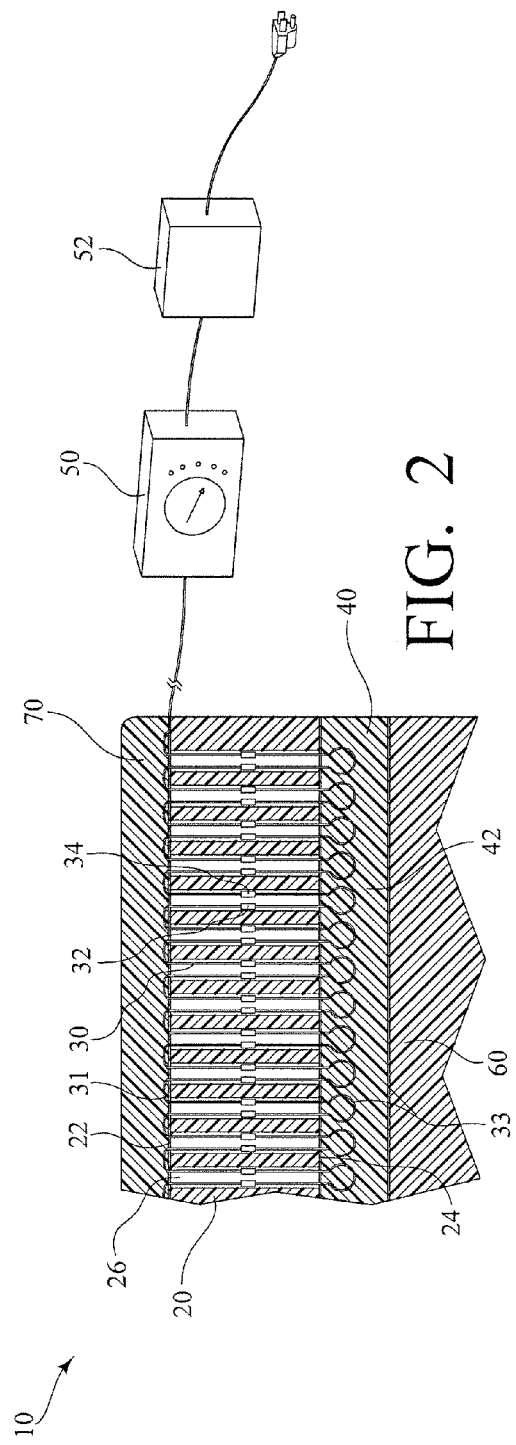

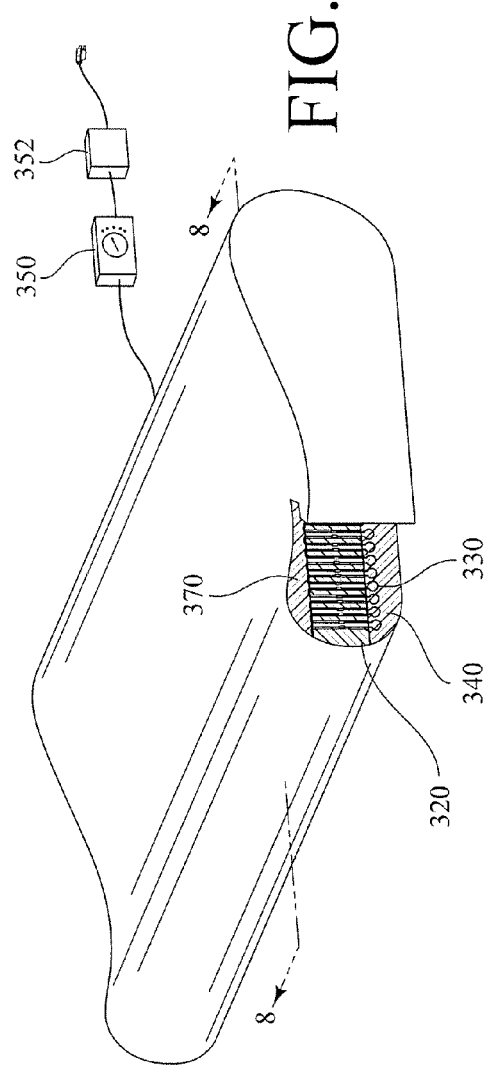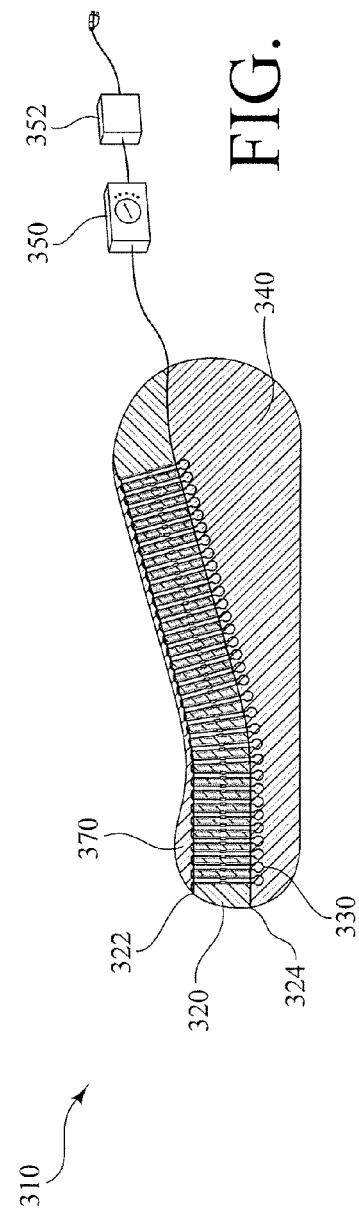

SUPPORT CUSHIONS AND METHODS FOR CONTROLLING SURFACE TEMPERATURE OF SAME

TECHNICAL FIELD

The present invention relates to support cushions and methods for controlling the surface temperature of support cushions. In particular, the present invention relates to support cushions, such as mattress assemblies, that make use of thermoelectric elements positioned and configured to selectively heat or cool the surfaces of the support cushions.

BACKGROUND

An aspect of successful and restful sleep is individual sleep comfort. Medical research suggests that sleep deprivation ("sleep debt") can have significant negative impacts on longevity, productivity, and overall mental, emotional, and physical health. Chronic sleep debt has been linked to weight gain and, more specifically, has been observed to not only affect the way the body processes and stores carbohydrates, but has also been observed to alter hormone levels that affect appetite. Moreover, sleep debt may result in irritability, impatience, inability to concentrate, and moodiness, which has led some researchers to suggest a link between sleep debt and worksite accidents, traffic incidents, and general afternoon inattentiveness. Furthermore, sleep disorders have been linked to hypertension, increased stress hormone levels, and irregular heartbeat, and additional research has recently suggested that a lack of sleep can affect immune function, resulting in increased susceptibility to illness and disease, e.g., cancer. In all, researchers have now suggested that sleep debt costs the United States $63 billion annually in lost productivity due to these various effects. Accordingly, a support cushion that improves sleep comfort and lowers individual sleep debt would be both highly desirable and beneficial.

SUMMARY

The present invention relates to support cushions and methods for controlling the surface temperature of a support cushion. In particular, the present invention relates to support cushions, such as mattress assemblies, that make use of thermoelectric elements positioned and configured to selectively heat or cool the surface of the support cushion. Thus, the support cushions of the present invention allow a user to individualize their level of comfort, including sleep comfort, by controlling the temperature of the surface of the support cushion.

In one exemplary embodiment of the present invention, a support cushion is provided in the form of a mattress assembly that includes a body supporting portion having a first surface and a second surface that is opposite the first surface. The mattress assembly further includes a plurality of thermoelectric elements that are positioned and configured to selectively provide heating or cooling at the first surface of the body supporting portion. The mattress assembly also includes a heat dissipating portion that is comprised of a thermally-absorbent material and is operably connected to the thermoelectric elements.

The body supporting portion of the mattress assembly is generally comprised of a flexible foam for suitably distributing pressure from a user's body or portion thereof across the body supporting portion. In some embodiments, the flexible foam is a visco-elastic foam that has a desired density and hardness, and allows pressure to be absorbed uniformly and distributed evenly across the body supporting portion of the mattress assembly. In this regard, in certain embodiments, the body supporting portion can be further covered by a comfort portion or layer that is positioned atop the body supporting portion to provide a level of comfort to a body of a user or a portion thereof that is resting on the mattress assembly. Such a comfort support portion, in certain embodiments, is also comprised of a visco-elastic foam or other foam, but typically has a density less than that of the body supporting portion of the mattress assembly so as to provide a softer surface on which to rest, and so as to provide a sufficiently soft barrier between the body of a user and the thermoelectric elements of the mattress assembly, as described in further detail below.

With respect to the thermoelectric elements of the mattress assembly, the thermoelectric elements are positioned in the mattress assembly and are configured to allow a user to control the temperature of the first (or upper) surface of the body supporting portion of the mattress assembly. For example, in certain embodiments, the thermoelectric elements are comprised of a plurality of Peltier elements that, upon flowing an amount of electrical current in a first direction through the Peltier elements, cool the first surface of the body supporting portion by drawing heat away from the first surface and toward the second surface of the body supporting portion. Similarly, in certain embodiments, upon flowing an amount of electrical current in a second (e.g., opposite) direction through the Peltier elements, the Peltier elements heat the first surface of the body supporting portion by drawing heat away from the second surface of the body supporting portion and toward the first surface of the body supporting portion.

To further take advantage of the heating and cooling capabilities of the Peltier elements, in certain embodiments, the Peltier elements are arranged in a series, such that the Peltier elements are arranged one after another and are capable of providing heating or cooling across the entire surface of the body supporting portion or a desired portion thereof. In other embodiments, the Peltier elements are arranged in an array, such that a group of Peltier elements can be positioned on a desired area of the body supporting portion and used to selectively heat or cool an area of the body supporting portion that would be in contact with a particular portion of the body of a user that is prone to excessive heating (e.g., the torso or head of a user). In some embodiments, to provide a greater amount of control over the selective heating and cooling of the first surface of the body supporting portion, the Peltier elements are comprised of discrete Peltier elements, are individually addressable, or both.

To facilitate the heating and cooling of the first surface of body supporting portion, each Peltier element typically spans the width of the body supporting portion of the mattress assembly, such that a first side of each Peltier element is positioned above or adjacent to the first surface of the body supporting portion and the opposite side of each Peltier element is positioned below or adjacent to the second surface of the body supporting portion. In these embodiments, the body supporting portion includes a plurality of columnar voids that each include a portion of the Peltier elements that are transmitting heat from one surface of the body supporting surface to the other. Thus, in certain embodiments, the Peltier elements are positioned adjacent to the body supporting portion and are directly transferring heat from one surface of the body supporting portion, through the interior of the body supporting portion, and to the other surface of the body supporting portion.

In addition to being configured to selectively heat or cool the first surface of the body supporting portion, the thermoelectric elements are also operably connected to a heat dissipating portion of the mattress assembly that is comprised of a thermally absorbent material. In some embodiments, the heat dissipating portion of the mattress assembly is comprised of an elastomeric gelatinous material that encases at least a portion of the Peltier elements adjacent to or near the second surface of the body supporting portion. By operably connecting the Peltier elements to the heat dissipating portion, the heat dissipating portion provides, in addition to structural support for the Peltier elements, a thermal dump or heat sink into which heat can be dissipated when the first surface of the body supporting portion is being cooled. Alternatively, when the first surface of the body supporting portion is being heated, the heat dissipating portion can also be used as a source of heat by transferring any collected heat in the heat dissipating portion to the first surface of the body supporting portion.

In some embodiments of the present invention, the heat dissipating portion is comprised of a substantially uniform layer of elastomeric gelatinous material. Such a substantially uniform layer of elastomeric gelatinous material is, in certain embodiments, used to cover the entirety of the second surface of the body supporting portion. In other embodiments that make use of an elastomeric gelatinous material, the heat dissipating portion is comprised of a plurality of three-dimensional blocks of elastomeric gelatinous material. In these embodiments, the three-dimensional blocks can be spaced at a predetermined distance from adjacent blocks of elastomeric gelatinous material, but are typically positioned adjacent to one or more of the plurality of Peltier elements to thereby provide individual heat sinks for each Peltier element, as opposed to providing a heat sink in the form of a continuous layer of elastomeric gelatinous material that is in contact with each of the Peltier elements included in the mattress assembly.

In yet further embodiments of the present invention, the heat dissipating portions are comprised of a thermally absorbent material that does not include an elastomeric gelatinous material. In one such embodiment, the heat dissipating portion is comprised of a fluid layer that, like the substantially uniform layer of elastomeric gelatinous material, is capable of serving as a heat sink when the first surface of the body supporting portion is being cooled, and is capable of acting as a source of stored heat when the first surface of the body supporting portion is to be heated. In other embodiments, the heat dissipating portion is comprised of a flexible foam that includes a plurality of cells having a reticulated cellular structure and that is operably connected to the Peltier elements such that the heat that is transferred from the first surface of the body supporting portion is transferred into the reticulated cellular structure. Upon transferring heat into the reticulated cellular structure, the heat can then be transferred out of the heat dissipating portion by conveying an amount of air through the reticulated cellular structure of the heat dissipating portion.

In certain embodiments of the mattress assemblies that make use of a reticulated cellular structure in the heat dissipating portion, the air is conveyed through the heat dissipating portion, at least in part, by including an inlet port and an outlet port in the heat dissipating portion to thereby provide a route through which air can flow into, through, and out of the heat dissipating portion. Moreover, in some embodiments, the heat can be forced to only flow through and out of certain portions of the heat dissipating layer by including a seal (i.e., a skin) that covers the outer surface of the heat dissipating portion. In such embodiments, the seal is used to effectively trap the heat in the heat dissipating portion until it is removed by conveying air through the reticulated cellular structure of the heat dissipating portion, such as by making use of inlet and outlet ports placed into the seal, by operably connecting fans to the heat dissipating portion to disperse the heat away, or both.

Regardless of the materials used for the heat dissipating portion, each mattress assembly of the present invention further includes a power supply for supplying electrical current to the plurality of thermoelectric elements, and a controller for controlling the electrical current that is supplied to the plurality of thermoelectric elements. By including a controller in the mattress assemblies, the amount of electrical current supplied to the thermoelectric elements can be controlled to provide a desired amount of heating or cooling to the first surface of the body supporting portion. For example, in certain embodiments, the controller is configured to automatically control the electrical current supplied to Peltier elements, such that the electrical current can be supplied to the Peltier elements in a particular direction to heat or cool the first surface of the body supporting portion when the first surface of the body supporting portion reaches a particular temperature. As another example, the controller, in some embodiments, is configured to allow the electrical current to be supplied to the Peltier elements for a predetermined time period, such as for an 8-hour sleeping period or for a length of time that corresponds to the time a user usually spends in a specific stage of the sleep cycle (e.g., REM sleep). In another example, the controller may receive biorhythm feedback from a user-worn sensor and coordinate operation of the Peltier elements accordingly.

To provide an additional level of control over the thermoelectric elements included in the mattress assemblies of the present invention, in certain embodiments, the mattress assemblies further include one or more features that are operably connected to the body supporting portion, the heat dissipating portion, or both of the mattress assembly and provide input to the controller. Such features include, in some embodiments, pressure sensors that provide pressure feedback to the controller and allow the controller to automatically begin heating or cooling the mattress assembly when a user lies on the mattress or otherwise places an amount of pressure on the mattress assembly. In other embodiments, temperature sensors are included in an exemplary mattress assembly and provide temperature feedback to the controller to allow the controller to selectively heat or cool the first surface of the body supporting portion in response to received temperature feedback and to maintain a desired temperature. Such desired temperature or pressure feedback settings are, in certain embodiments, directly inputted or adjusted at the controller itself or, in other embodiments, can be transmitted to the controller from a remote control that is also operably connected to the controller and allows a user to remotely adjust the first surface of the body supporting portion to a desired temperature.

To further obtain some of the benefits associated with incorporating a plurality of thermoelectric elements into a mattress assembly, in some embodiments, the thermoelectric elements incorporated into the mattress assembly are positioned and configured to convert a temperature difference between the body supporting portion and the heat dissipating portion into an electric voltage at a charging port. Such an embodiment has essentially the same structural configuration as the embodiments described above, with the substitution of the charging port in lieu of the controller, power supply, or both. The charging port is operably connected to the thermoelectric elements such that, when a temperature difference exists between the body supporting portion and the heat dissipating portion, an electric voltage is generated at the charging port, which can then be used to charge a battery (e.g., a battery of an electronic device such as a cellular telephone, portable music player, alarm clock, portable computing device, etc.).

As an additional refinement to the mattress assemblies of the present invention, in some embodiments, mattress assemblies are provided that include additional features to further increase the comfort and convenience of the user of the mattress assembly. For example, as described above, each of the mattress assemblies of the present invention generally includes at least two portions or layers, namely a body supporting portion or layer and a heat dissipating portion or layer. In some embodiments, however, additional layers are incorporated into the mattress assemblies to provide an increased level of comfort, to provide additional support for the mattress assemblies, or both. For instance, in certain embodiments, a base portion or layer is included in the mattress assembly to provide support to the body supporting portion, the heat dissipating portion, or both. In some embodiments, the base portion is adjustable to allow a user to place the mattress assembly into one or more desired ergonomic positions.

With further regard to the support cushions of the present invention, an exemplary support cushion can also be used as part of a method of controlling a surface temperature of a support cushion. In some implementations, a method of controlling the surface temperature of a support cushion includes first providing a support cushion having a body supporting portion, a heat dissipating portion comprised of an elastomeric gelatinous material, and a plurality of Peltier elements positioned in the support cushion and operably connected to the body supporting portion and the heat dissipating portion. Electrical current is then supplied to the plurality of Peltier elements, such that when electrical current is supplied in a first direction, the surface temperature of the body supporting portion decreases, or such that when electrical current is supplied in a second direction, the surface temperature of the body supporting portion increases. Any heat generated by supplying electrical current to the plurality of Peltier elements is subsequently dissipated into the heat dissipating portion that, by virtue of the elastomeric gelatinous material, acts as a thermal dump or heat sink and allows the body supporting portion to be cooled without the use of fans or other similarly noisy devices that are commonly used to dissipate heat away from a support cushion and into the surrounding atmosphere.

Further features and advantages of the present invention will become evident to those of ordinary skill in the art after a study of the description, figures, and non-limiting examples in this document.

BRIEF DESCRIPTION OF THE DRAWINGS

FIG. 1 is a perspective view of an exemplary support cushion, in the form of a mattress assembly, made in accordance with the present invention;

FIG. 2 is a partial cross-sectional view of the exemplary mattress assembly of FIG. 1 taken along line 2-2 of FIG. 1;

FIG. 7 is a perspective view of an exemplary support cushion, in the form of a pillow, made in accordance with the present invention, with a portion of the pillow cut away to show Peltier elements positioned adjacent to the various layers of the pillow;

FIG. 8 is a cross-sectional view of the exemplary pillow shown in FIG. 7 taken along line 8-8 of FIG. 7;

DESCRIPTION OF EXEMPLARY EMBODIMENTS

Figure 3:
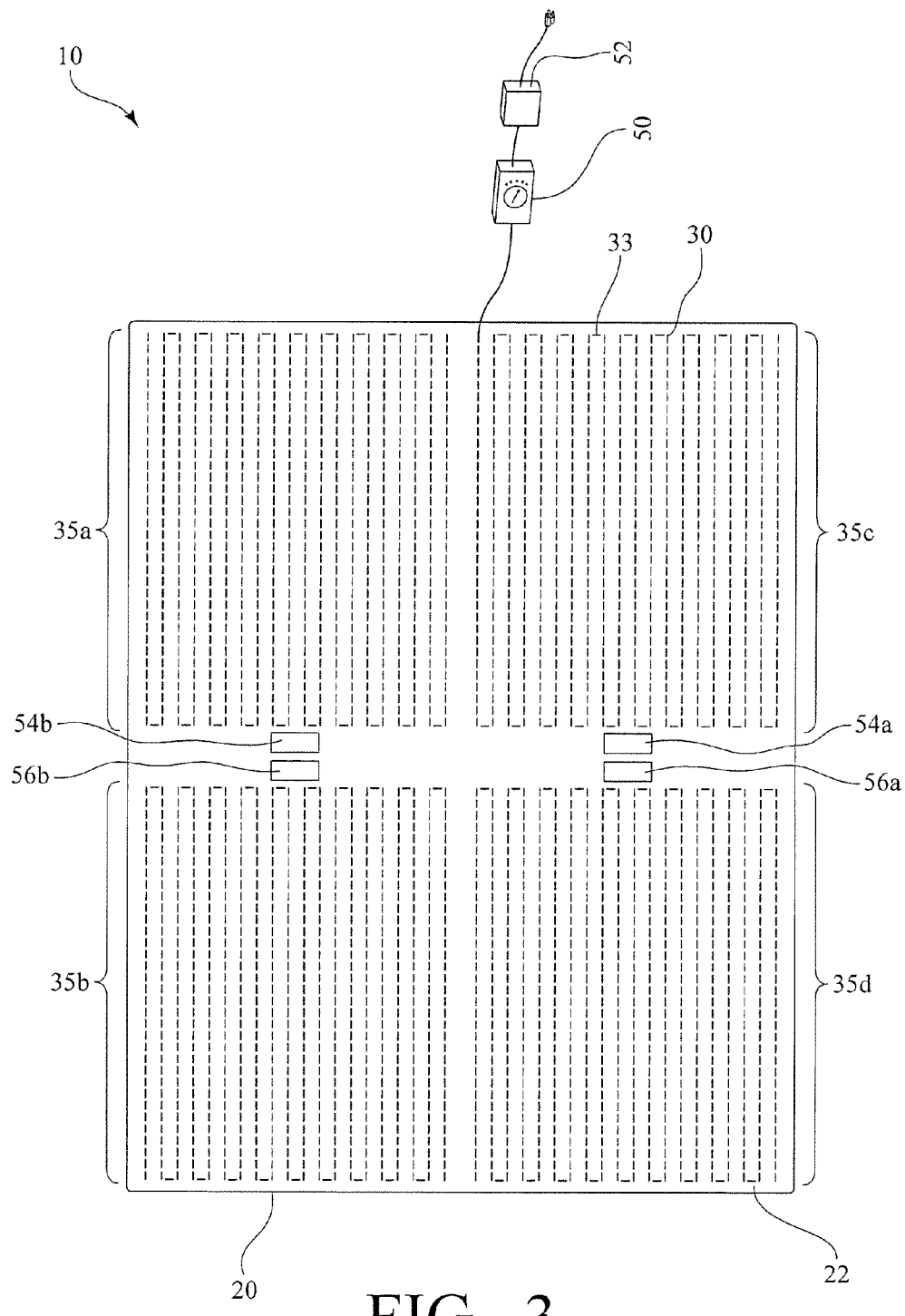
FIG. 3 is another cross-sectional view of the exemplary mattress assembly of FIG. 1, but taken along line 3-3 of FIG. 1.

The present invention relates to support cushions and methods for controlling the surface temperature of a support cushion. In particular, the present invention relates to support cushions, such as mattress assemblies, that include a plurality of thermoelectric elements operably connected to a heat dissipating portion that is comprised of a thermally absorbent material. The support cushions of the present invention allow a user to control the temperature of the surface of the support cushion without also requiring the use of a fan or similar device to dissipate heated or cooled air generated by the thermoelectric elements away from the support cushion and into the surrounding atmosphere. Thus, the support cushions of the present invention allow a user to individualize their level of comfort, including sleep comfort, by controlling the temperature of the surface of the support cushion, and allow a user to do so in a manner that lacks the noise of conventional systems that make use of fans or other similar devices.

Referring first to FIGS. 1-4, in one exemplary embodiment of the present invention, a support cushion in the form of a mattress assembly 10 is provided that includes a body supporting portion 20 having a first surface 22, which is generally an upper surface of the body supporting portion 20, and a second surface 24, which is generally the lower surface of the body supporting portion 20 and is opposite the first surface 22. The mattress assembly 10 further includes a plurality of thermoelectric elements in the form of Peltier elements 30 that are positioned in the body supporting portion 20 and are configured to selectively provide heating or cooling at the first surface 22 of the body supporting portion 20. Also included in the mattress assembly 10 is a heat dissipating portion 40 that is comprised of a thermally-absorbent material and is operably connected to the Peltier elements 30.

The body supporting portion 20 of the mattress assembly 10 is generally comprised of a continuous layer of flexible foam for suitably distributing pressure from a user's body or portion thereof across the body supporting portion 20. Such flexible foams include, but are not limited to, latex foam, reticulated or non-reticulated visco-elastic foam (sometimes referred to as memory foam or low-resilience foam), reticulated or non-reticulated non-visco-elastic foam, polyurethane high-resilience foam, expanded polymer foams (e.g., expanded ethylene vinyl acetate, polypropylene, polystyrene, or polyethylene), and the like. In the embodiment shown in FIGS. 1-4, the body supporting portion 20 is comprised of a visco-elastic foam that has a low resilience as well as a sufficient density and hardness, which allows pressure to be absorbed uniformly and distributed evenly across the body supporting portion 20 of the mattress assembly 10. Generally, such visco-elastic foams have a hardness of at least about 10 N to no greater than about 80 N, as measured by exerting pressure from a plate against a sample of the material to a compression of at least 40% of an original thickness of the material at approximately room temperature (i.e., 21° C. to 23° C.), where the 40% compression is held for a set period of time as established by the International Organization of Standardization (ISO) 2439 hardness measuring standard. In some embodiments, the visco-elastic foam has a hardness of about 10 N, about 20 N, about 30 N, about 40 N, about 50 N, about 60 N, about 70 N, or about 80 N to provide a desired degree of comfort and body-conforming qualities.

The visco-elastic foam described herein for use in the mattress assembly 10 can also have a density that assists in providing a desired degree of comfort and body-conforming qualities, as well as an increased degree of material durability. In some embodiments, the density of the visco-elastic foam used in the body supporting portion 20 has a density of no less than about 20 kg/m$^3$ to no greater than about 150 kg/m$^3$. In some embodiments, the density of the visco-elastic foam used in the body supporting portion 20 of the mattress assembly 10 is about 20 kg/m$^3$, about 30 kg/m$^3$, about 40 kg/m$^3$, about 50 kg/m$^3$, about 60 kg/m$^3$, about 70 kg/m$^3$, about 80 kg/m$^3$, about 90 kg/m$^3$, about 100 kg/m$^3$, about 110 kg/m$^3$, about 120 kg/m$^3$, about 130 kg/m$^3$, about 140 kg/m$^3$, or about 150 kg/m$^3$. Of course, the selection of a visco-elastic foam having a particular density will affect other characteristics of the foam, including its hardness, the manner in which the foam responds to pressure, and the overall feel of the foam, but it is appreciated that a visco-elastic foam having a desired density and hardness can readily be selected for a particular application or mattress assembly as desired. Additionally, it is appreciated that the body supporting portions of the mattress assemblies need not be comprised of a continuous layer of flexible foam at all, but can also take the form of more traditional mattresses, including spring-based mattresses, without departing from the spirit and scope of the subject matter described herein.

Referring still to FIG. 1, the body supporting portion 20 of the mattress assembly 10 is further covered by a comfort portion or layer 70 that is positioned atop the body supporting portion 20 and provides a level of comfort to a body of a user or a portion of thereof that is resting on the mattress assembly 10. The comfort layer 70 can also be comprised of a visco-elastic foam. However, the comfort layer 70 typically has a density, hardness, or both that is less than that of the body supporting portion 20 of the mattress assembly 10, such that the comfort layer 70 provides a softer surface on which to rest the body of a user or a portion thereof, while also providing a sufficiently soft barrier between the body of a user and the Peltier elements 30 of the mattress assembly 10, as described in further detail below. For example, in certain embodiments, the mattress assembly 10 includes a body supporting portion 20 that is comprised of visco-elastic foam with a density of about 75 kg/m$^3$ and a hardness of about 13 N, while the comfort layer is comprised of a visco-elastic foam with a density of about 35 kg/m$^3$ and a hardness of about 10 N.

Regardless of the particular densities of the body supporting portion 20 and the comfort layer 70, the body supporting portion 20 and the comfort layer 70 are generally secured to one another to prevent the body supporting portion 20 and the comfort layer 70 from moving relative to one another during use. Various means of securing one layer of material to another can be used in this regard, including tape, hook and loop fasteners, conventional fasteners, stitches, and the like. In one particular embodiment, the body supporting portion 20 and the comfort layer 70 are bonded together by an adhesive or cohesive bonding material to create a substantially continuous assembly where the body supporting portion 20 and the comfort layer 70 are fully adhered to one another. Such adhesive bonding materials include, for example, environmentally-friendly, water based adhesives, like SABA AQUA-BOND RSD, a two-component water-based adhesive product produced by SABA DINXPERLO BV, B-7090 AA, Dinxperlo, Belgium.

With further regard to the body supporting portion 20 shown in FIGS. 1-4, the body supporting portion 20 generally has a composition different than that of the heat dissipating portion 40 of the mattress assembly 10, as is described in further detail below, but it is additionally contemplated that an exemplary body supporting portion can be further comprised of one or more different or additional layers having various densities and hardnesses. For instance, it is contemplated that a layer of high-resilience polyurethane foam can be secured to the second surface of a layer of low-resilience visco-elastic foam used in a body supporting portion. Such multi-layered body supporting portions are described, for example, in U.S. Pat. Nos. 7,469,437; 7,507,468; 8,025,964; and 8,034,445, as well as in U.S. Patent Application Publication No. 2011/0252562, each of which is incorporated herein by this reference.

Turning now to the thermoelectric elements included in the support cushions of the present invention, various thermoelectric elements can be incorporated into a support cushion and used to heat or cool a surface of an exemplary support cushion, including resistive heaters that convert electrical energy to heat, as well as other thermoelectric elements. In the exemplary mattress assembly 10 shown in FIGS. 1-4, and as indicated above, the thermoelectric elements are Peltier elements 30 that are positioned in the mattress assembly 10 and are configured to allow a user to control the temperature of the first surface 22 of the body supporting portion 20 of the mattress assembly 10, which can then change the temperature of the comfort layer 70 of the mattress assembly 10 by virtue of the proximity of the first surface 22 of the body supporting portion 20 to the comfort layer 70. The Peltier elements 30, which may also be referred to as Peltier devices, Peltier heaters or heat pumps, solid-state refrigerators or thermoelectric heat pumps, are solid-state active heat pumps which transfer heat from one side of body supporting portion 20 of the mattress assembly 10 to the other side of the body supporting portion 20 by flowing an amount of electrical current through the Peltier elements 30 to produce a Peltier effect or, in other words, the presence of heat at an electrified junction of two different metals.

In the Peltier elements 30 shown in FIGS. 1-4, the junctions of two different metals are in the form of a n-type semiconductor or element 32 and a p-type semiconductor or element 34. In these Peltier elements 30, when an amount of electrical current flows in a first direction through the n-type element 32, crosses a metallic interconnect 33, and passes into the p-type element 34, a Peltier effect is created whereby electrons in the n-type elements 32 move in the opposite direction of the current and holes in the p-type element 34 move in the direction of current, such that both remove heat from the first surface 22 of the body supporting portion 20 of the mattress assembly 10 toward the second surface 24 of the body supporting portion 20. Similarly, with the Peltier elements 30, upon flowing an amount of electrical current in a second (e.g., opposite) direction through the Peltier elements 30 and the n-type elements 32 and p-type elements 34, the Peltier effect can be reversed, and the Peltier elements 30 can be used to heat the first surface 22 of the body supporting portion 20 by drawing heat away from the second surface 24 of the body supporting portion 20 and toward the first surface 22 of the body supporting portion 20.

As shown in FIG. 2, to facilitate the heating and cooling of the first surface 22 of body supporting portion 20, the Peltier elements 30 substantially span the width of the body supporting portion 20 of the mattress assembly 10 such that an upper portion 31 of each of the Peltier elements 30 is positioned above and adjacent to the first surface 22 of the body supporting portion 20, and the metallic interconnects 33 of the Peltier elements 30 are positioned below and adjacent to the second surface 24 of the body supporting portion 20. To allow the Peltier elements 30 to pass through the body supporting portion 20, the body supporting portion 20 includes a plurality of columnar voids 26 where parts of the body supporting portion 20 have been removed to allow a portion of the Peltier elements 30, including the n-type elements 32 and the p-type elements 34 to be positioned in and pass through the body supporting portion 20 and allow heat to be transferred from one surface of the body supporting portion 20 to the other. In other words, and as best shown in FIG. 2, the Peltier elements 30 are positioned adjacent to the body supporting portion 20 and direct transfer heat from one surface of the body supporting portion 20 and through the body supporting portion 20 to the other surface of the body supporting portion 20.

Figure 4:
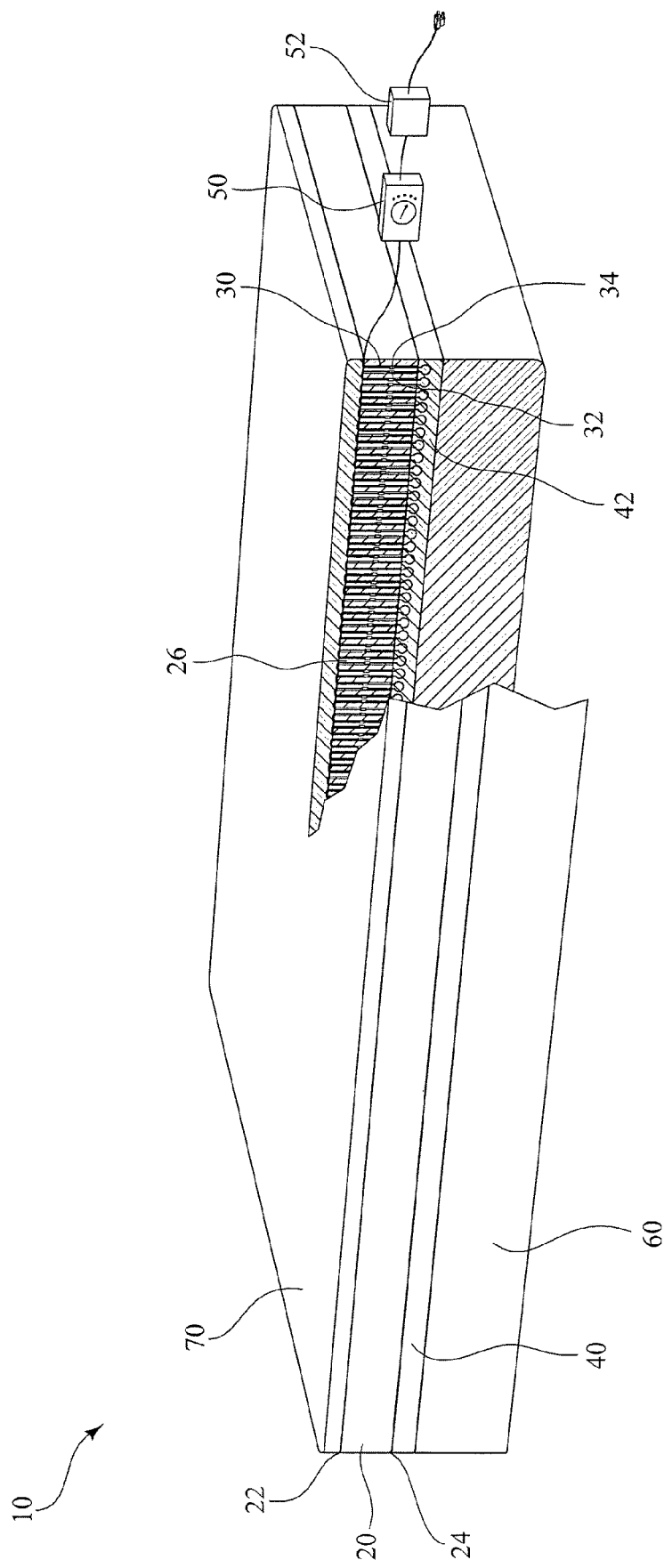
FIG. 4 is a perspective view of the exemplary mattress assembly similar to that of FIG. 1, but with a portion of the mattress assembly removed to show a plurality of Peltier elements positioned adjacent to the various layers of the mattress assembly.

Referring now to FIGS. 2-4, to further take advantage of the heating and cooling capabilities of the Peltier elements 30, the Peltier elements 30 are arranged in a series, where the Peltier elements 30 are arranged one after another to provide substantially uniform and continuous heating or cooling across the entire first surface 22 of the body supporting portion 20 or a portion thereof. In this regard, and as best shown in FIG. 3, the Peltier elements 30 are further arranged in arrays 35a, 35b, 35c, 35d, such that groupings of Peltier elements 30 are positioned on certain areas of the body supporting portion 20 and used to selectively heat or cool an area of the body supporting portion 20. Each such area would be in contact with a particular portion of the body of a user that is prone to excessive heating or cooling (e.g., the torso or head of a user vs. the legs of a user). For example, and as described in further detail below, in some embodiments, the arrays 35a, 35b, 35c, 35d of Peltier elements 30 are individually addressable such that it is possible to cool the arrays 35a, 35c that would be in contact with the torso or head of a user lying in a supine or prone position, while heating the arrays 35b, 35d that would be in proximity to the legs of a user lying in a supine or prone position. Of course, to provide a greater amount of control over the selective heating and cooling of the first surface 22, individual rows or columns of the Peltier elements 30 in the arrays 35a, 35b, 35c, 35d can also be individually addressable such that more specific portions of the first surface 22 of the body supporting portion 20 can be selectively heated and cooled to allow a particular portion of a user's body to be heated or cooled, or to allow only the Peltier elements 30 that are in closest contact with the body of a user to be selectively heated or cooled (e.g., when a user is lying on their side). Likewise, although not shown in FIGS. 2-4, it is also appreciated that the Peltier elements used in the mattress assemblies of the present invention can be provided in the form of discrete Peltier elements that are not connected to one another in a series, so as to provide an even greater amount of control over the heating and cooling of the first surface of a body supporting portion.

Referring now to FIGS. 1, 2, and 4, in addition to being configured to selectively heat or cool the first surface 22 of the body supporting portion 20, the Peltier elements 30 are also operably connected to the heat dissipating portion 40 of the mattress assembly 10. Such a heat dissipating portion 40 is comprised of a thermally absorbent material. More particularly, in the embodiment shown in FIGS. 1, 2, and 4, the heat dissipating portion 40 of the mattress assembly 10 is comprised of a substantially uniform layer of elastomeric gelatinous material that is secured to and covers the entirety of the second surface 24 of the body supporting portion 20. The elastomeric gelatinous material of the heat dissipating portion 40 also encases the metallic interconnects 33 of the Peltier elements 30 near the second surface 24 of the body supporting portion 20. In this regard, by operably connecting the Peltier elements 30 to the heat dissipating portion 40, the heat dissipating portion 40 provides, in addition to structural support for the Peltier elements 30, a thermal dump or heat sink into which heat can be dissipated when the first surface 22 of the body supporting portion 20 is being cooled. Alternatively, when the first surface 22 of the body supporting portion 20 is being heated, the heat dissipating portion 40 can also be used as a source of heat by transferring any collected heat in the heat dissipating portion 40 from the heat dissipating portion 40 to the first surface 22 of the body supporting portion 20. As such, the heat dissipating portion 40 allows, at least in part, the first surface 22 of the body supporting portion 20 of the mattress assembly 10 to be selectively heated and cooled without requiring a fan or other similar device to vent the heat byproducts of the Peltier effect into the surrounding atmosphere, and without also requiring a separate heat source to supply heat to the first surface 22 of the body supporting portion 20.

Figure 5:
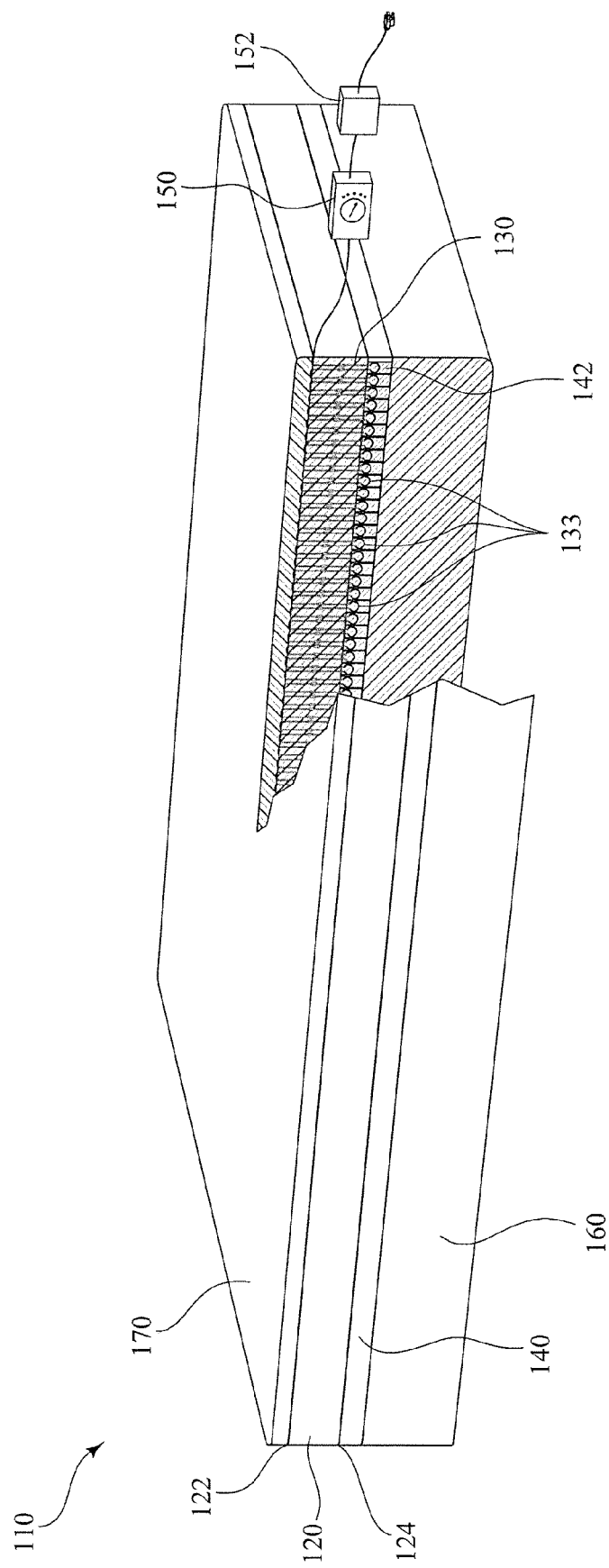
FIG. 5 is a perspective view of another exemplary support cushion, in the form of a mattress assembly, made in accordance with the present invention, with a portion of the mattress assembly removed to show Peltier elements positioned adjacent to the various layers of the mattress assembly.
Figure 6:
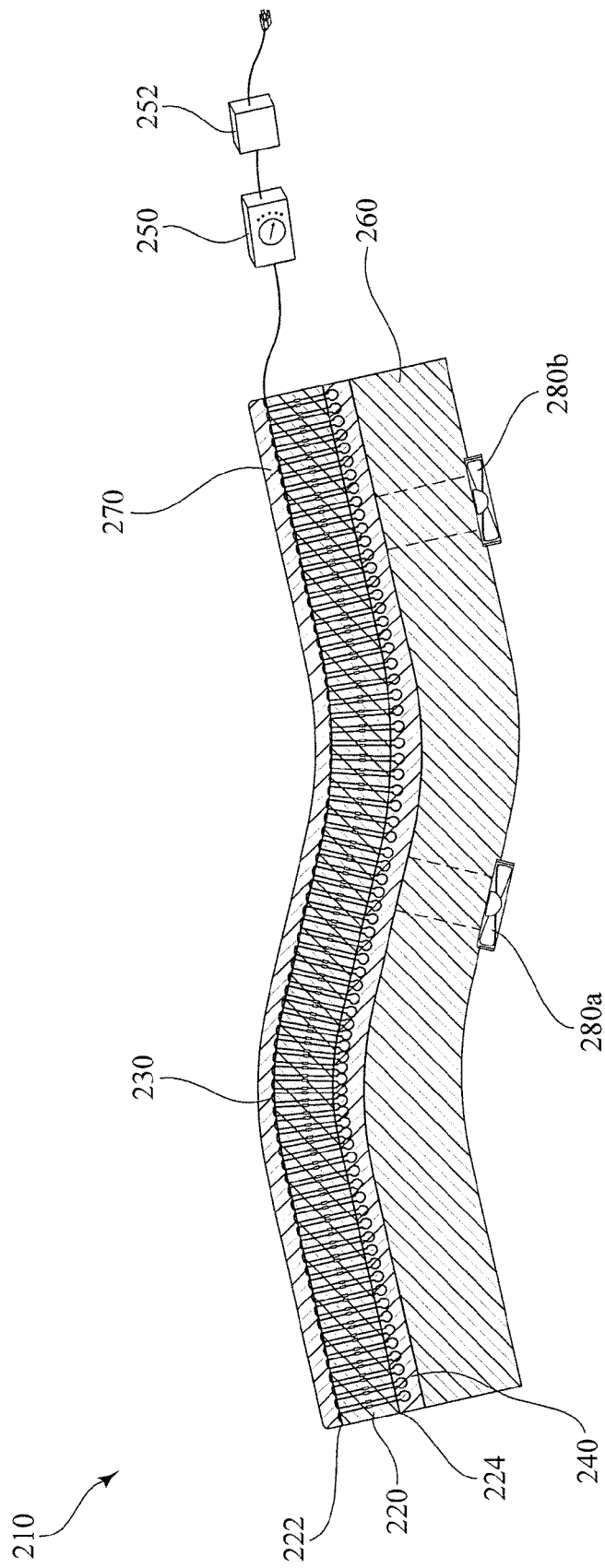
FIG. 6 is a cross-sectional view of yet another exemplary support cushion, in the form of a mattress assembly, made in accordance with the present invention, and showing the mattress assembly having an adjustable base layer and a pair of fans positioned in the mattress assembly.

As a refinement, in another embodiment of the present invention that makes use of an elastomeric gelatinous material as a thermal dump or heat sink, and referring now to FIG. 5, an exemplary mattress assembly 110 is provided that includes a comfort layer 170, a body supporting portion 120 having a first surface 122 and a second surface 124, a plurality of Peltier elements 130, and a heat dissipating portion 140 that includes an elastomeric gelatinous material. Unlike the mattress assembly 10 shown in FIGS. 1-4, however, the elastomeric gelatinous material included in the heat dissipating layer 140 is not in the form of a substantially continuous layer, but is instead in the form of three-dimensional blocks 142 of elastomeric gelatinous material. Each of the blocks 142 of elastomeric gelatinous material can be spaced at a predetermined distance from adjacent blocks 142, but are, in generally positioned such that the blocks 142 each encase the metallic interconnects 133 of the Peltier elements 130 and thereby provide individualized heat sinks for the Peltier elements 130.

Heat dissipating portions having various other configurations or comprised of various other materials that are capable of serving as a heat sink when the first surface of an exemplary body supporting portion is being cooled and that are also capable of acting as a source of heat when the first surface of a body supporting portion is being heated, such fluid layers and the like, can also be included in a mattress assembly or other support cushion made in accordance with the present invention. For example, as another refinement to the heat dissipating portion of the mattress assemblies of the present invention, and referring now to FIGS. 11 and 12, an exemplary mattress assembly 610 is provided that includes a comfort layer 670, a body supporting portion 620 having a first surface 622 and a second surface 624, a plurality of Peltier elements 630, each of which is positioned in a columnar void 626 of the body supporting portion 620, and a heat dissipating portion 640. Unlike the heat dissipating portions 40, 140 shown in FIGS. 1-5, however, the heat dissipating portion 640 is not comprised of an elastomeric gelatinous material, but is comprised of a flexible foam that includes a plurality of cells having a reticulated cellular structure and that is operably connected to the Peltier elements 630, such that the heat that from the first surface 622 of the body supporting portion 620 can be transferred into the reticulated cellular structure of the heat dissipating portion 640.

Reticulated foam (visco-elastic or otherwise) is a cellular foam structure in which the cells of the foam are essentially skeletal. In other words, the cells of the reticulated foam are each defined by a plurality of apertured windows surrounded by cell struts, where the cell windows of reticulated foam can be entirely absent (leaving only the cell struts) or substantially missing. In some embodiments, the foam is considered "reticulated" if at least 50% of the windows of the cells are missing (i.e., windows having apertures therethrough, or windows that are completely missing and therefore leaving only the cell struts). Such structures can be created by destruction or other removal of cell window material, by chemical or mechanical means, or by preventing the complete formation of cell windows during the manufacturing process of the foam.

Regardless of the manufacturing process used to produce the reticulated foam, reticulated foam, by virtue of its reticulated cellular structure, has characteristics that are well suited for use in the heat dissipating portion 640 of the mattress assembly 610, including the enhanced ability to permit fluid movement through the reticulated foam and, consequently, the ability to provide enhanced air and/or heat movement within, through, and away from the body supporting portion 620 and the comfort layer 670 of the mattress assembly 610. In this regard, by encasing the metallic interconnects 633 in the reticulated foam of the heat dissipating portion 640, the heat that is transferred to the heat dissipating layer 640 by the Peltier elements 630 as part of the cooling of the first surface 622 of the body supporting portion 620 is allowed to easily disperse throughout the reticulated foam of the heat dissipating portion 640. Upon transferring heat into the reticulated cellular structures, the heat can then easily be transferred out of the heat dissipating portion 640 by conveying an amount of air through the reticulated cellular structure of the heat dissipating portion 640.

Figure 11:
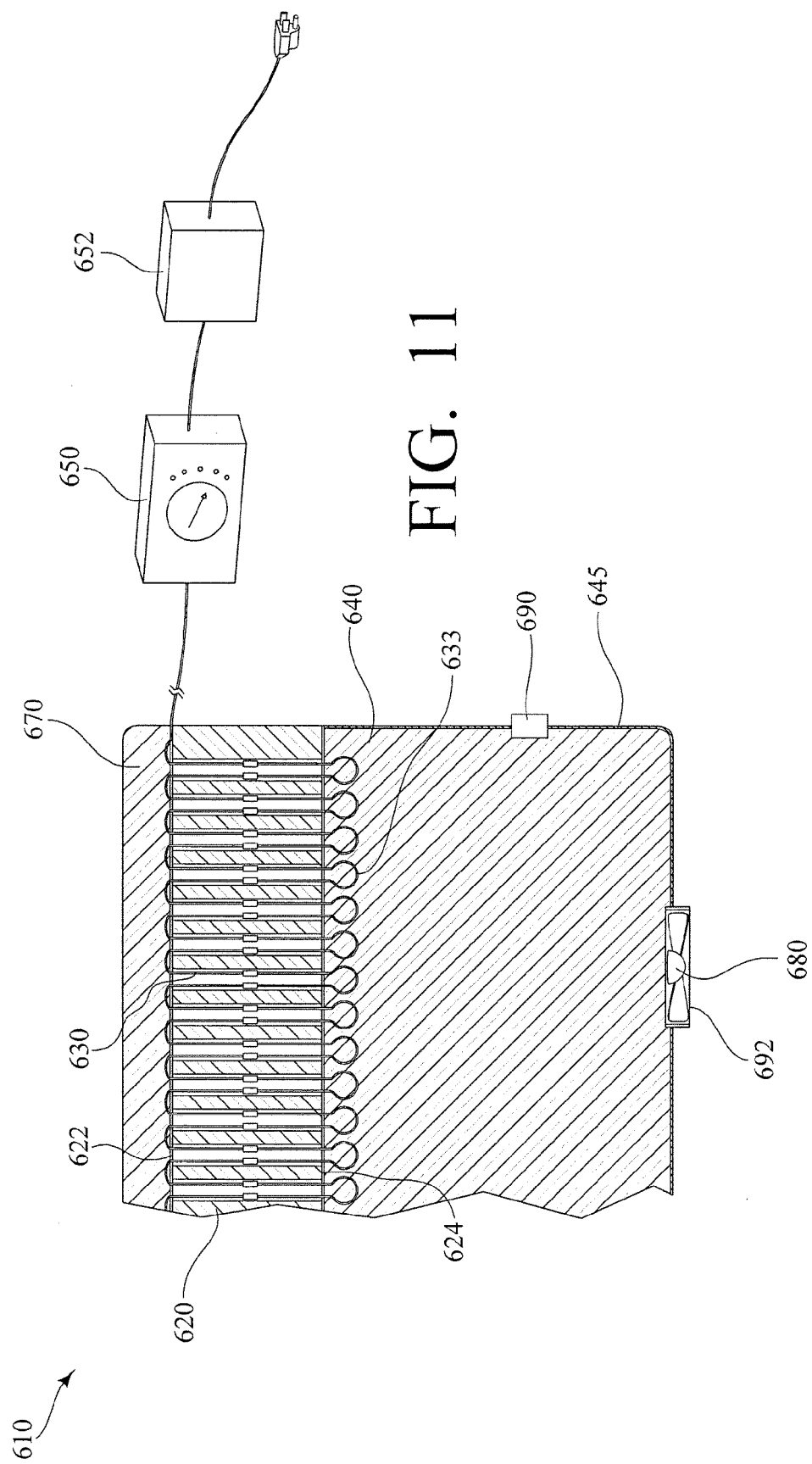
FIG. 11 is a cross-sectional view of yet another exemplary support cushion, in the form of a mattress assembly, made in accordance with the present invention, and showing a plurality of Peltier elements positioned adjacent to a heat dissipating portion that includes a plurality of foam cells having a reticulated cellular structure.
Figure 12:
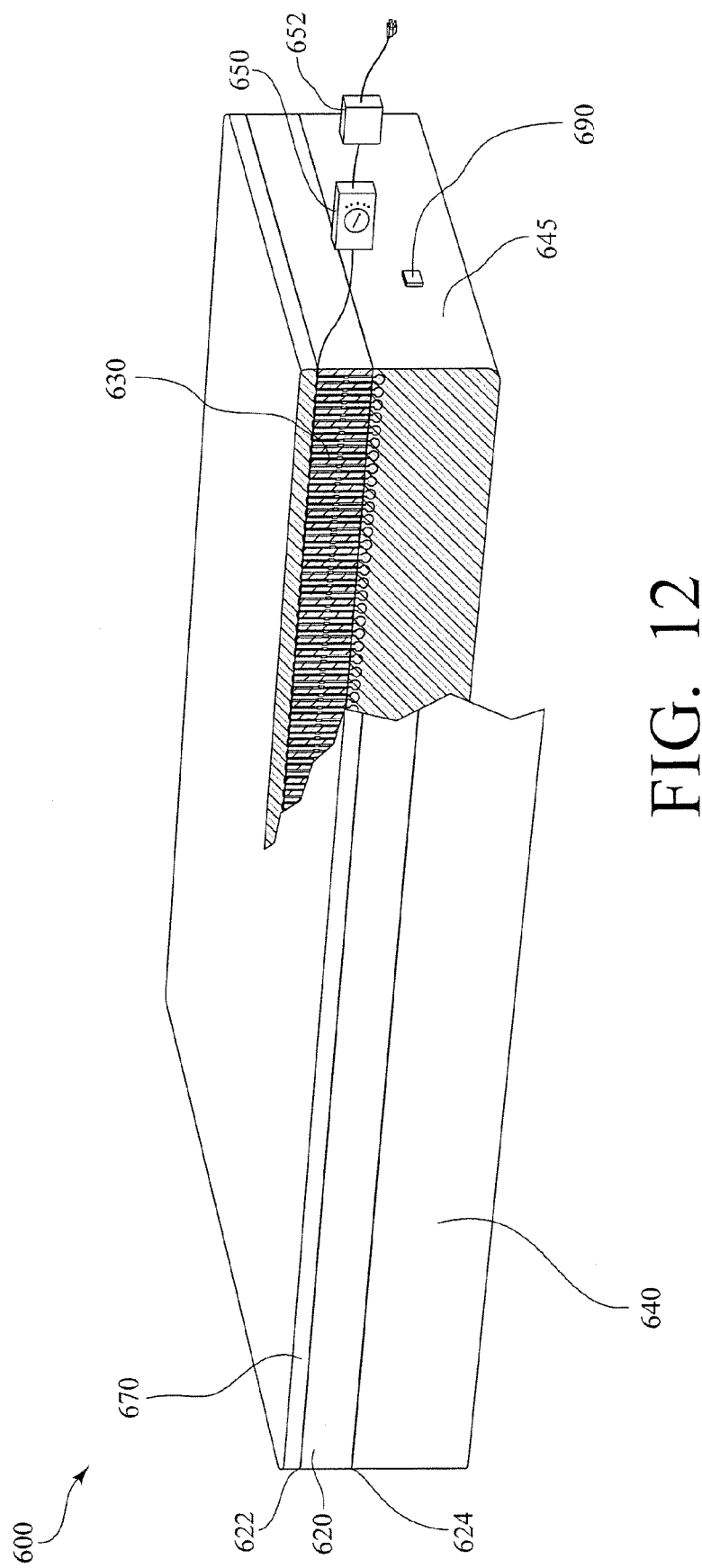
FIG. 12 is a perspective view of the exemplary mattress assembly of FIG. 11, but with a portion of the mattress assembly removed to show the plurality of Peltier elements positioned adjacent to the heat dissipating portion.

To assist in conveying air through the heat dissipating portion 640 of the mattress assembly 610, in one exemplary embodiment and referring still to FIGS. 11 and 12, the heat dissipating portion 640 includes an inlet port 690 and an outlet port 692 that are included in the heat dissipating portion 640 to provide a route through which air can flow through the heat dissipating portion 640. Moreover, in the mattress assembly 610, the heat that is transferred into the heat dissipating portion 640 from the Peltier elements 630 during the cooling of the first surface 622 of the body supporting portion 620 can be forced to only flow out of certain portions of the heat dissipating layer by the inclusion of a seal 645 (i.e., a skin) that covers the heat dissipating portion 640 and effectively traps the heat in the heat dissipating portion 640 and prevents it from flowing back into the body supporting portion 620. By including the seal 645, the heat can then only be removed by conveying air through the reticulated cellular structure of the heat dissipating portion 640, either by making use of the inlet port 690 and outlet port 692 that are cut into the seal 645, by making use of a fan 680 that is operably connected to the outlet port 692, or both. Such a seal 645 can created by making use of a poured flexible foam where the foam is produced by pouring its components into a mold and allowing them to set. Of course, various other skins or seals, such as seals that are comprised of nylon polyurethane materials and are commonly used as mattress covers, may also be used as seals or outer coverings for the heat dissipating portion 640 without departing from the spirit and scope of the subject matter described herein.

Referring now to FIGS. 1-6 and 11-12, regardless of the materials used for the heat dissipating portion 40, 140, 640, each mattress assembly 10, 110, 610 of the present invention further includes a power supply 52, 152, 652 for supplying electrical current to the plurality of Peltier elements 30, 130, 630, as well as a controller 50, 150, 650 for controlling the electrical current that is supplied to the plurality of Peltier elements 30, 130, 630. By including a controller 50, 150, 650 in the mattress assemblies 10, 110, 610, the amount of electrical current supplied to the Peltier elements 30, 130, 630 can be controlled to provide a desired amount of heating or cooling to the first surface 22, 122, 622 of each mattress assembly 10, 110, 610. For example, the controller 50, 150, 650 can be configured to automatically control the electrical current supplied to Peltier elements 30, 130, 630, such that electrical current can be supplied to the Peltier elements 30, 130, 630 to heat or cool the first surface 22, 122, 622 of each body supporting portion 20, 120, 620 when the first surface 22, 122, 622 of the body supporting portion 20, 120, 620 reaches a particular temperature, such as after a user has been lying on the body supporting portion 20, 120, 620 for an extended period of time. As another example, the controllers 50, 150, 650 can also be configured to allow the electrical current to be supplied to the Peltier elements for a predetermined time period, such as for an 8-hour sleeping period.

As yet another example, the controllers 50, 150, 650 can further be configured to supply electrical current to the Peltier elements 30, 130, 630 in a manner that corresponds to a user's sleep rhythms. For instance, it is appreciated that during REM (rapid eye movement) sleep, a user generally loses at least some of their ability to control the temperature of his or her body. As such, in certain embodiments, the controllers 50, 150, 650 can be configured to begin cooling the first surfaces 22, 122, 622 of the body supporting portions 20, 120, 620 at a time during the course of a night's sleep when a user would generally be in REM sleep. Alternatively, the controllers 50, 150, 650 can further be operably connected to a device that monitors sleep rhythms, such as, for example, the ZEO SLEEP MANAGER™ manufactured by ZEO, Newton, Mass., such that the controllers 50, 150, 650 can be configured to provide electrical current to the Peltier elements 30, 130, 630 upon receiving input that the user lying on the mattress assembly 10, 110, 610 has entered a particular stage of the sleep cycle (e.g., REM sleep).

In addition to providing control over the amount of current that is being supplied to the Peltier elements 30, 130, 630, the controllers 50, 150, 650 of the mattress assemblies 10, 110, 610 further allow the direction of the electrical current being supplied to the Peltier elements 30, 130, 630 to be controlled. In this regard, the controllers 50, 150, 650 can be used to alter the direction of the electrical current being supplied to the Peltier elements 30, 130, 630 to either selectively heat or cool the first surfaces 22, 122, 622 of the body supporting portions 20, 120, 620 of the mattress assemblies 10, 110, 610, but can further be configured to dissipate heat from the heat dissipating portions 40, 140, 640 of the mattress assemblies 10, 110, 610 after an extended period of cooling the first surfaces 22, 122, 622 of the body supporting portions 20, 120, 620. For instance, after an overnight period of cooling the first surfaces 22, 122, 622 of the body supporting portions 20, 120, 620, a significant amount of heat will have been transferred to the heat dissipating portions 40, 140, 640 of the mattress assemblies 10, 110, 610. As such, to dissipate that heat and release it from the heat dissipating portions 40, 140, 640, the direction of the electrical current being supplied to the Peltier elements 30, 130, 630 can be reversed, and the heat in the heat dissipating portions 40, 140, 640 can be transferred from the heat dissipating portions 40, 140, 640 to the first surfaces 22, 122, 622 of the body supporting portions 20, 120, 620 and released into the surrounding atmosphere.

Figure 10:
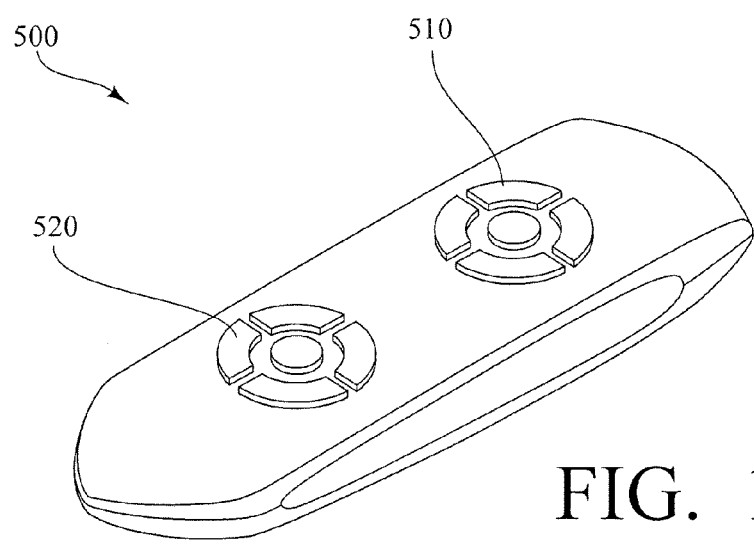
FIG. 10 is perspective view of an exemplary remote control for controlling the surface temperature of a support cushion made in accordance with the present invention.

To provide an additional level of control over the Peltier elements 30, 130, 630 included in the mattress assemblies 10, 110, 610 of the present invention, the mattress assemblies 10, 110, 610 can further include one or more features that are operably connected to the body supporting portions 20, 120, 620, the heat dissipating portions 40, 140, 640, or both of the mattress assemblies 10, 110, 610 and provide input to the controllers 50, 150, 650. For example, and referring now to FIG. 3, the mattress assembly 10 includes pressure sensors 54a, 54b that provide pressure feedback to the controller 50 in response to a user resting upon the first surface 22 of the body supporting portion 20 to thereby allow the controller 50 to automatically begin providing electrical current and heating or cooling the mattress assembly 10 as soon as the user lies on the mattress assembly 10 or otherwise places an amount of pressure on the mattress assembly 10. As also shown in FIG. 3, temperature sensors 56a, 56b are further included in the mattress assembly 10 and provide temperature feedback to the controller 50 to thereby allow the controller to selectively heat or cool the first surface of the mattress assembly 10 in response to the received temperature feedback and to thereby maintain a desired temperature at the first surface 22 of the body supporting portion 20. Such desired temperature or pressure feedback settings are, in certain embodiments, directly inputted or adjusted at the controller 50 itself or, in other embodiments, are transmitted to the controller 50 from a remote control 500 that includes temperature control buttons 510, as shown in FIG. 10, and that is also operably connected to the controller 50.

Figure 13:
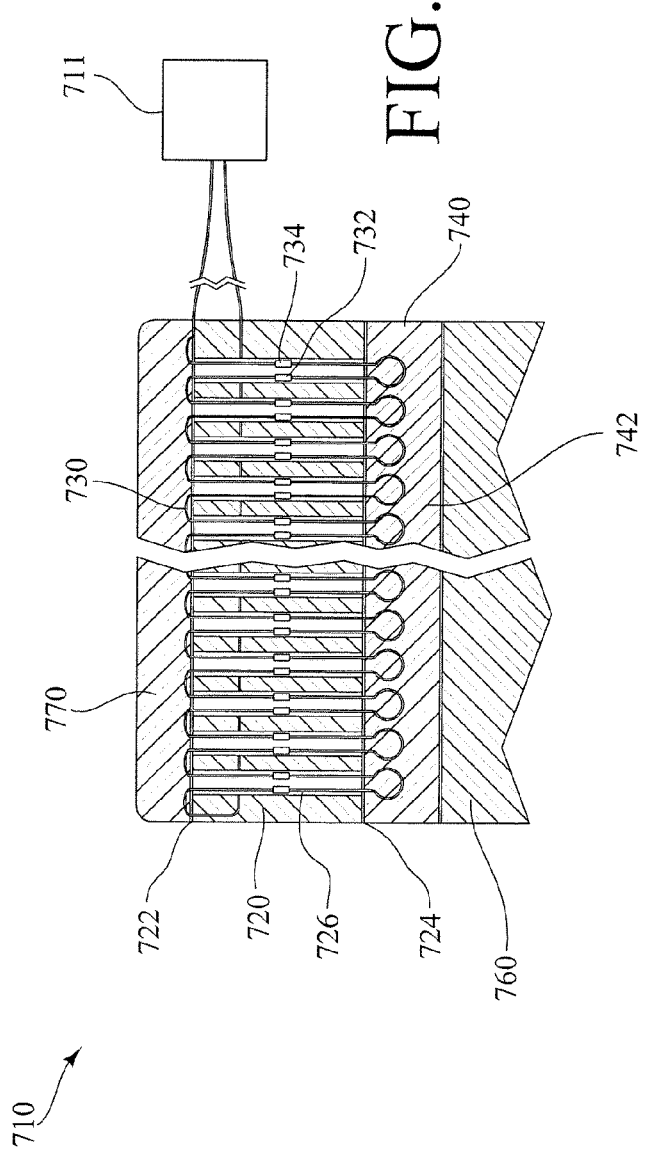
FIG. 13 is a cross-sectional view of a further exemplary support cushion, in the form of a mattress assembly, made in accordance with the present invention and including a charging port.
Figure 14:
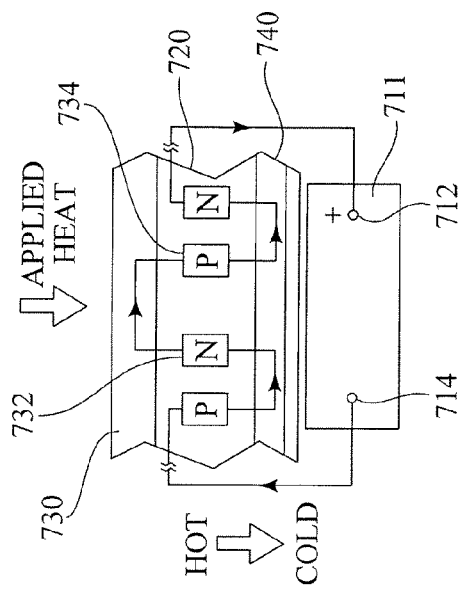
FIG. 14 is a schematic diagram of a circuit of the exemplary mattress assembly of FIG. 13.

As a further refinement to the use of thermoelectric elements in accordance with the present invention, in some embodiments, the thermoelectric elements of the support cushions can be used not only to selectively heat and cool the support cushion, but can further be used to convert thermal energy into electrical energy. Referring now to FIGS. 13 and 14, in another exemplary embodiment, a support cushion 710 includes a plurality of Peltier elements 730 that are positioned in a body supporting portion 720 and are configured to convert a temperature difference between the body supporting portion 720 and a heat dissipating portion 740 into an electric voltage at a charging port 711. The support cushion 710 has essentially the same structural configuration of body supporting portion 720, heat dissipating portion 740, and Peltier elements 730 as the embodiments described above, and it should be understood that the detailed description of the basic structural configuration of the above embodiments applies equally to the support cushion 710, where similar elements are identified according to a corresponding labeling convention (e.g., 20-720, 22-722, 24-724, etc.). Notably, however, the support cushion 710 further includes the charging port 711 operably connected to the Peltier elements 730 such that when a temperature difference exists between the body supporting portion 720 and the heat dissipating portion 740, thermal energy from the body supporting portion 720 drives electrons in the n-type element 732 toward the cooler heat dissipating portion 740, which creates a current while holes in the p-type element 734 flow in the direction of the current and an electric voltage is subsequently generated at the charging port 711. The electric voltage at the charging port 711 can then be used to charge a battery (e.g., a battery of an electronic device such as a cellular telephone, portable music player, alarm clock, portable computing device, etc.).

Referring more specifically now to FIG. 14, FIG. 14 is a schematic diagram of a circuit of the exemplary support cushion 710, where an electric voltage is generated at terminals 712, 714 of the charging port 711, and where a Seebeck effect is created by the circuit. The Seebeck effect is the conversion of temperature differences directly into electricity caused by charge-carrier diffusion and phonon drag when conductors or semi-conductors having different thermal properties are connected. Of course, it is understood that the Seebeck effect illustrated in FIG. 14, with the "applied heat" and the "hot-to-cold" directional indicators resulting in the current flow and voltage shown, could easily be reversed. In this regard, it is possible that the thermal energy stored in a heat dissipating portion of a support cushion of the present invention, such as the thermal energy that is created and stored following an extended period of cooling at the first surface of the body supporting portion, could be converted to an electrical voltage and subsequently used to charge a battery.

As yet another refinement to the mattress assemblies of the present invention, the mattress assemblies 10, 110 further include a base portion or layer 60, 160 that provides support to the body supporting portion 20, 120 and the heat dissipating portion 40, 140, as shown in FIGS. 1-5 and 11-12. In a further exemplary embodiment, however, and referring now to FIG. 6, a mattress assembly 210 is provided that includes additional features in the base layer 260 to increase the comfort and convenience of the user of the mattress assembly 210. Like the mattress assemblies shown in FIGS. 1-5 and 11-12, the mattress assembly 210 includes a comfort layer 270, a body supporting portion 220 having a first surface 222 and a second surface 224, a plurality of Peltier elements 230 operably connected to a controller 250 and a power supply 252, and a heat dissipating layer 240. The base portion or layer 260 that provides support to the body supporting portion 220 and the heat dissipating portion 240, however, is adjustable to allow a user to place the mattress assembly 210 into one or more desired ergonomic positions. Additionally, included in the base portion 260 of the mattress assembly 210 are two fans 280a, 280b that are operably connected to heat dissipating portion 240 and are capable of assisting in dissipating heat generated as a result of the Peltier effect to thereby supplement the heat capturing properties of the heat dissipating portion 240 and provide greater control over the selective heating and cooling of the first surface 222 of the body supporting portion 220. In some embodiments, the base layer 260 and fans 280a, 280b can be adjusted or utilized by changing the settings of the base layer 260 or fans 280a, 280b directly on the controller 250 or, alternatively, can be adjusted or utilized by making use of base layer and fan control buttons 520 on the remote control 500 shown in FIG. 5.

Figure 9:
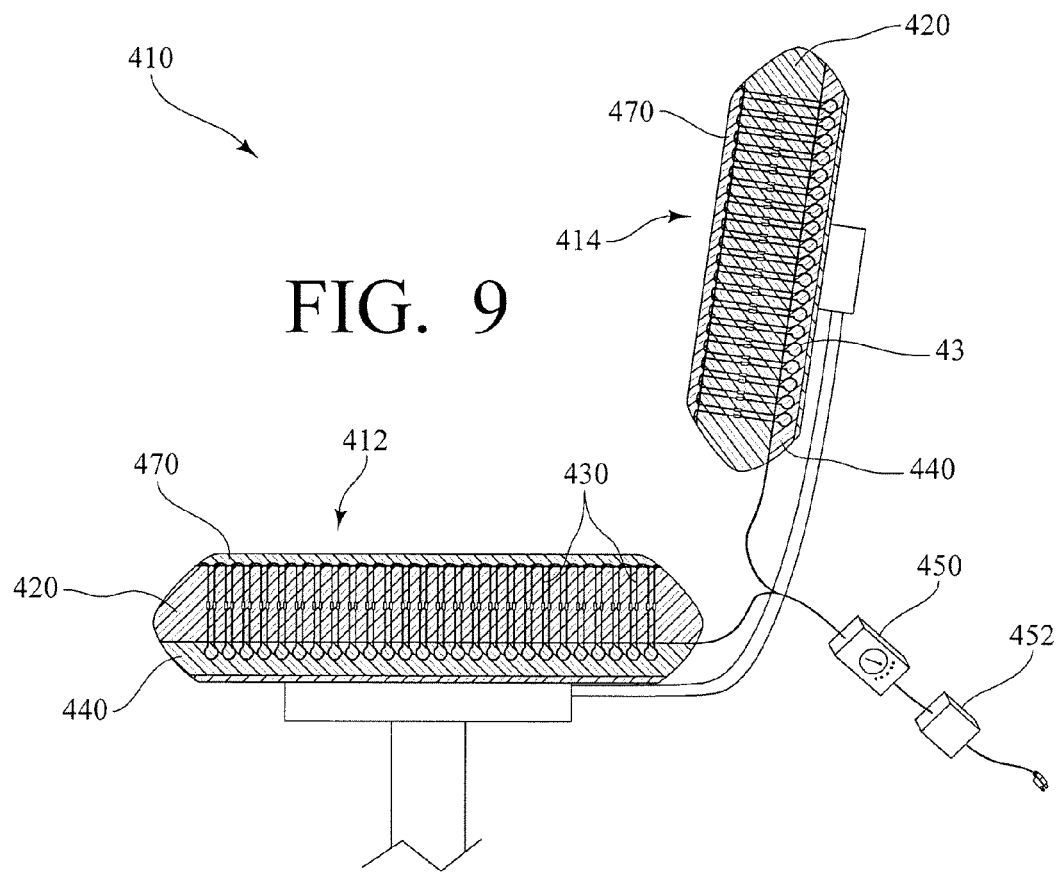
FIG. 9 is a cross-sectional view of exemplary support cushions for use in a chair and made in accordance with the present invention, and showing a plurality of Peltier elements positioned adjacent to the various layers of the support cushions.

As an even further refinement to the present invention, although the support cushions shown in FIGS. 1-6 and 11-14 are in the form of mattress assemblies 10, 110, 210, 610, 710, and are dimensionally sized to support a user lying in a supine or prone position, it is contemplated that the features described herein are equally applicable to head pillows, seat cushions, seat backs, neck pillows, leg spacer pillows, mattress toppers, overlays, and the like. As such, the phrase "body support" or "body supporting" is used herein to refer to any and all such objects having any size or shape, and that are capable of or are generally used to support the body of a user or a portion thereof. For example, as shown in FIGS. 7 and 8, in an additional exemplary embodiment of the present invention, a support cushion in the form a contoured neck pillow 310 is provided that includes a comfort layer 370, a head and neck supporting layer 320, a plurality of Peltier elements 330 operably connected to a controller 350 and a power supply 352, and a heat dissipating portion 340 to assist in the selective heating and cooling of the supporting layer 320 and the comfort layer 370. Similarly, as shown in FIG. 9 and as another example, support cushions made in accordance with the present invention are incorporated into the seat 412 and the back 414 of a desk chair 410. Each support cushion of the desk chair 410 includes a comfort layer 470, a body supporting layer 420, a plurality of Peltier elements 430 operably connected to a controller 450 and a power supply 452, and a heat dissipating portion 440 to assist in the selective heating and cooling of the seat 412 and the back 414 of the desk chair 410.

Each of the exemplary support cushions described herein can also be used as part of a method of controlling a surface temperature of a support cushion. In some implementations, a method of controlling the surface temperature of a support cushion includes first providing a support cushion of the present invention. Electrical current is then supplied to the plurality of Peltier elements, such that when electrical current is supplied in a first direction, the surface temperature of the body supporting portion decreases, but when electrical current is supplied in a second direction, the surface temperature of the body supporting portion increases. Then, any heat generated by supplying electrical current to the plurality of Peltier elements is dissipated into the heat dissipating portion that acts as a thermal dump or heat sink to allow the body supporting portion to be cooled without the use of fans or other similarly noisy devices to dissipate the heat into away from the support cushion and into the surrounding atmosphere. In some embodiments, heat is further dissipated away from the heat dissipating portion by conveying air through the heat dissipating portion and/or by activating one or more fans operably connected to the heat dissipating portion to thereby dissipate heat away from the heat dissipating portion. In some embodiments, the surface temperature of the support cushion is controlled by first receiving feedback from a temperature or pressure sensor positioned in the body supporting portion of the support cushions, and then supplying electrical current to a plurality of Peltier elements incorporated into the support cushion, either in a first or second direction, based on the feedback received from the temperature sensor, the pressure sensor, or both.

Throughout this document, various references are mentioned. All such references are incorporated herein.

One of ordinary skill in the art will recognize that additional embodiments are also possible without departing from the teachings of the present invention or the scope of the claims which follow. This detailed description, and particularly the specific details of the exemplary embodiments disclosed herein, is given primarily for clarity of understanding, and no unnecessary limitations are to be understood therefrom, for modifications will become apparent to those skilled in the art upon reading this disclosure and may be made without departing from the spirit or scope of the claimed invention.

What is claimed is:

1. A support cushion, comprising:
a body supporting portion having a first surface and a second surface opposite the first surface;
a plurality of thermoelectric elements positioned and configured to selectively provide heating or cooling at the first surface of the body supporting portion, the plurality of thermoelectric elements including metallic interconnects positioned below the second surface of the body supporting portion; and
a heat dissipating portion comprised of a thermally-absorbent elastomeric gelatinous material, the thermally-absorbent elastomeric gelatinous material operably connected to the thermoelectric elements and positioned below the second surface of the body supporting portion, wherein the metallic interconnects extend into the thermally-absorbent elastomeric gelatinous material, and wherein all surfaces of the metallic interconnects positioned below the second surface of the body supporting portion are in full contact with thermally-absorbent elastomeric gelatinous material.

2. The support cushion of claim 1, wherein the heat dissipating portion comprises a plurality of three-dimensional blocks of elastomeric gelatinous material, each block of elastomeric gelatinous material spaced at a predetermined distance from each adjacent block of elastomeric gelatinous material, and each block of elastomeric gelatinous material positioned adjacent to one or more of the plurality of thermoelectric elements.

3. The support cushion of claim 1, wherein the heat dissipating portion comprises a substantially uniform layer of elastomeric gelatinous material.

4. The support cushion of claim 1, wherein the body supporting portion is comprised of a material different from the thermally absorbent material of the heat dissipating portion.

5. The support cushion of claim 1, wherein the body supporting portion is comprised of a flexible foam.

6. The support cushion of claim 1, wherein the body supporting portion is comprised of a visco-elastic foam.

7. The support cushion of claim 1, wherein the body supporting portion is dimensionally-sized to support a user lying in a supine or prone position.

8. The support cushion of claim 1, wherein the plurality of thermoelectric elements is positioned adjacent to the body supporting portion.

9. The support cushion of claim 1, wherein the thermoelectric elements are discrete Peltier elements.

10. The support cushion of claim 1, wherein the plurality of thermoelectric elements are multiple Peltier elements arranged in a series.

11. The support cushion of claim 1, wherein the thermoelectric elements are arranged in an array.

12. The support cushion of claim 11, wherein at least a portion of the thermoelectric elements of the array are individually addressable.

13. The support cushion of claim 1, wherein the body supporting portion includes a plurality of columnar voids, and wherein each columnar void includes at least a portion of one thermoelectric element.

14. The support cushion of claim 1, further comprising a power supply for supplying electrical current to the thermoelectric elements, and further comprising a controller for controlling the electrical current supplied to the thermoelectric elements from the power supply.

15. The support cushion of claim 14, wherein the controller is configured to automatically control the electrical current supplied to the thermoelectric elements.

16. The support cushion of claim 14, wherein the controller is configured to allow electrical current to be supplied to the thermoelectric elements for a predetermined time period.

17. The support cushion of claim 14, further comprising a temperature sensor for providing thermal feedback to the controller, the temperature sensor operably connected to the body supporting portion, the heat dissipating portion, or both.

18. The support cushion of claim 14, further comprising a pressure sensor for providing pressure feedback to the controller, the pressure sensor operably connected to the body supporting portion, the heat dissipating portion, or both.

19. The support cushion of claim 1, further comprising one or more fans operably connected to the heat dissipating portion for dissipating heat away from the heat dissipating portion.

20. The support cushion of claim 1, further comprising a base portion positioned to provide support to the body supporting portion, the heat dissipating portion, or both.

21. A support cushion, comprising:
a first layer having a first surface and a second surface opposite the first surface;
a plurality of Peltier elements positioned and configured to selectively provide heating or cooling at the first surface of the first layer, the plurality of Peltier elements including metallic interconnects positioned below the second surface of the first layer; and
a second layer comprised of a thermally-absorbent elastomeric gelatinous material, the second layer positioned below the first layer, wherein the metallic interconnects extend into the thermally-absorbent elastomeric gelatinous material, and wherein all surfaces of the metallic interconnects positioned below the second surface of the first layer are in full contact with the thermally-absorbent elastomeric gelatinous material such that the second layer of thermally-absorbent elastomeric gelatinous material absorbs heat generated by the plurality of Peltier elements when the Peltier elements are providing cooling of the first layer.

22. A mattress assembly, comprising:
a mattress having an upper surface and a lower surface opposite the upper surface;
a plurality of Peltier elements positioned and configured to selectively provide heating or cooling at the upper surface, the plurality of Peltier elements including metallic interconnects positioned below the lower surface of the mattress; and
a layer of thermally-absorbent elastomeric gelatinous material, the layer of thermally-absorbent elastomeric gelatinous material positioned below the lower surface of the mattress, wherein the metallic interconnects extend into the layer of thermally-absorbent elastomeric gelatinous material, and wherein all surfaces of the metallic interconnects positioned below the lower surface of the mattress are in full contact with the thermally-absorbent elastomeric gelatinous material such that the layer of thermally-absorbent elastomeric gelatinous material provides a heat sink for heat generated by the plurality of Peltier elements when the Peltier elements are providing cooling of the upper surface of the mattress.

23. The mattress assembly of claim 22, wherein the mattress is comprised of a visco-elastic foam.

24. The mattress assembly of claim 22, further comprising a comfort layer positioned atop the mattress, the comfort layer being comprised of a visco-elastic foam.

25. The mattress assembly of claim 24, wherein the comfort layer has a density less than that of the mattress.

26. The mattress assembly of claim 22, wherein the layer of thermally-absorbent elastomeric gelatinous material comprises a substantially uniform layer of elastomeric gelatinous material.

27. The mattress assembly of claim 22, further comprising a base layer positioned and configured to provide support to the mattress, the layer of thermally-absorbent elastomeric gelatinous material, or both.

28. The mattress assembly of claim 27, wherein the base layer is adjustable.

* * * * *